United States Patent [19]

Wang

[11] Patent Number: 5,001,213

[45] Date of Patent: * Mar. 19, 1991

[54] THERMOSETTING RESIN COMPOSITIONS

[75] Inventor: Pen-Chung Wang, Houston, Tex.

[73] Assignee: Shell Oil Company, Houston, Tex.

[*] Notice: The portion of the term of this patent subsequent to Jun. 12, 2007 has been disclaimed.

[21] Appl. No.: 474,954

[22] Filed: Feb. 5, 1990

Related U.S. Application Data

[63] Continuation-in-part of Ser. No. 334,406, Apr. 7, 1989, Pat. No. 4,933,423.

[51] Int. Cl.$^5$ ...................... C08G 59/26; C08G 59/06
[52] U.S. Cl. .......................................... 528/96; 528/99
[58] Field of Search .............................. 528/96; 529/99

[56] References Cited

U.S. PATENT DOCUMENTS

| | | | |
|---|---|---|---|
| 3,388,098 | 6/1968 | Harding | 528/96 |
| 3,401,147 | 9/1968 | Smith et al. | 528/96 |
| 4,487,915 | 12/1984 | Hefner, Jr. | 528/96 |
| 4,532,308 | 7/1985 | Sato et al. | 528/96 X |
| 4,656,294 | 4/1987 | Kanayama | 529/96 X |
| 4,895,942 | 1/1990 | Wang | 540/489 |

*Primary Examiner*—Earl Nielsen

[57] ABSTRACT

Novel thermosetting resin compositions comprise a mixture of the epoxyalkylether of a 1,6-diazo[4.4]-spirodilactam having a hydroxyaryl substituent on each of the spiro ring nitrogen atoms, and at least one amine compound. The cured compositions obtained by heating the resin compositions to an elevated temperature have relatively high glass transition temperatures and good physical properties.

18 Claims, No Drawings

THERMOSETTING RESIN COMPOSITIONS

CROSS-REFERENCE TO RELATED APPLICATIONS

This application is a continuation-in-part of U.S. Pat. application Ser. No. 334,406, filed April 7, 1989, now Pat. No. 4,933,423, issued June 12, 1990.

FIELD OF THE INVENTION

This invention relates to novel thermosetting resin compositions and to the cured products obtained by the heating thereof. More particularly, the invention relates to thermosetting resin compositions comprising (1) a diglycidyl ether of a hydroxyaryl-substituted 1,6-diaza [4.4] spirodilactam having a hydroxyaryl substituent on each spiro ring nitrogen atom and (2) at least one amine compound.

BACKGROUND OF THE INVENTION

The curing of monomeric materials to produce thermoset resins is well known in the art. In general, the polymerizable monomers have at least one and customarily more than one reactive group which serves as a site for a curing or crosslinking reaction. The resulting cured products are typically highly crosslinked, insoluble solids. There are some polymerizable monomeric materials which will cure upon application of energy, e.g., heat or UV light. In many if not most cases, however, the addition of a curing agent is necessary to allow the crosslinking reaction to proceed at an acceptable rate. The curing agents are catalytic or stoichiometric relative to the resin to the crosslinked. The stoichiometric curing agents, a term often applied to a curing agent which is employed in a substantial quantity relative to the resin, are the more commonly used and are typically multi-functional compounds having a plurality of reactive sites capable of participating in crosslinking reactions. A mixture of the resin and a curing agent, referred to as a thermosetting resin composition, is then cured by application of heat, with or without the presence of an accelerator which may be added to obtain a more acceptable rate.

The class of chemical compounds known as epoxies, epoxides or oxirane compounds has well established utility in the art as the precursor of thermoset resins. Such compounds are characterized by the presence within the molecule of at least one oxacyclopropane group, i.e., the

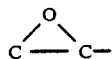

group. The reactive oxygen-containing three-membered ring provides an active site through which polymerization takes place. Polyfunctional epoxides including diglycidyl ethers of dihydroxylic compounds or diglycidyl esters of dibasic acids are broadly known in the art as is the reaction of such epoxides with active hydrogen compounds such as polyfunctional acids or amines. The resulting polymeric products are thermoset resins of known commercial utility in adhesives, films and coatings. By way of a particular illustration, the diglycidyl ether of 2,2-di(4-hydroxyphenyl)propane, also referred to as bisphenol A or BPA, is an epoxy compound of substantial commercial utility. It is marketed by Shell Chemical Company as EPON® 828 Resin and is also marketed by others.

The polyfunctional epoxides of cyclic structure are of particular importance because of the relatively high glass transition temperatures which their cured derivatives often exhibit. It would be of advantage to provide novel thermosetting resins which include resin components having a number of types of cyclic structure.

SUMMARY OF THE INVENTION

This invention provides novel thermosetting resin compositions comprising epoxyalkyl derivatives of certain 1,6-diaza [4.4] spirodilactams having hydroxyaryl substituents on each spiro ring nitrogen atom. More particularly, the invention relates to the thermosetting resin compositions comprising such epoxyalkyl derivatives and amine compounds, as well as to cured, thermoset resin products prepared therefrom.

DESCRIPTION OF THE INVENTION

The invention comprises thermosetting resin compositions of certain amine compounds and epoxyalkyl ethers of a hydroxyaryl-substituted 1,6-diaza [4.4] spirodilactam wherein the hydroxyaryl-containing substituents are located on the spiro ring nitrogen atoms. Although a wide variety of such substituted spirodilactams are suitable as the precursor of the epoxy-containing component of the compositions of the invention, the preferred hydroxyaryl-substituted spirodilactams have up to 60 carbon atoms and are represented by the formula

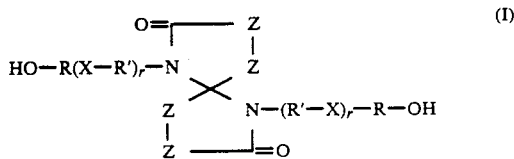

wherein Z independently is $>C(Z')_2$ in which Z' is hydrogen, lower alkyl of up to 4 carbon atoms inclusive, preferably methyl, or halo, preferably the lower halogens, fluoro or chloro, aryl, preferably phenyl, or Z' is such that two adjacent Z groups taken together form a ring system Z" of from 5 to 7 ring atoms, up to two of which are heteroatoms selected from nitrogen, oxygen or sulfur with the remainder of the ring atoms being carbon atoms, these being up to 15 carbon atoms in each Z", two of which form a bridge between the keto and spiro carbon atoms connected by the adjacent Z groups. In the above formula 1, R independently is aromatic of up to 15 carbon atoms and up to 2 aromatic rings, inclusive, R' independently is R or aliphatic of up to 10 carbon atoms inclusive, X is a direct valence bond, alkylene of up to 8 carbon atoms inclusive, oxy, thio, sulfonyl, carbonyl, dioxyphenylene, 2,2-di(oxyphenyl)-propane, di(oxyphenyl)sulfone or dioxydiphenylene and r independently is 0 or 1. R and R' independently are hydrocarbyl containing only atoms of carbon and hydrogen or are substituted hydrocarbyl containing additional atoms such as halogen, preferably the middle halogens, chloro or bromo, which are present as inert monovalent carbon atom substituents.

The various modifications of the hydroxyaryl-substituted spirodilactams of the above formula I will be apparent from the formula and the description of the components thereof. However, by way of further illustration, in the embodiment wherein the Z moieties are acyclic, i.e., each Z is >C(Z')$_2$, the substituted spirodilactams are illustrated by 1,6-di(4-hydroxyphenyl)-1,6-diazaspiro[4.4]nonane-2,7-dione, 1,6-di(3-hydroxy-4-chlorophenyl)-3,8-dimethyl-1,6-diazaspiro[4.4]nonane-2,7-dione, 1,6-di [4-(4-hydroxyphenyloxy)phenyl]-1,6-diazaspiro[4.4]nonane-2,7-dione, 1,6-di[4(3-hydroxybenzoyl)]phenyl-1,6-diazaspiro[4.4]nonane-2,7-dione, 1,6-di(4-hydroxyphenyl)-3,3,4,4,8,8,9,9-octamethyl-1,6-diazaspiro[4.4]nonane-2,7-dione, 1,6-di[4(4'-hydroxybiphenyl)]-3,3-dimethyl-1,6-diazaspiro[4.4]nonane-2,7-dione, 1,6-di[2-(4-hydroxyphenyl)propyl]-1,6-diazaspiro[4.4]nonane-2,7-dione, and 1,6-di(4-hydroxyphenyl)-3,4,8,9-tetrafluoro-1,6-diazaspiro[4.4]nonane-2,7-dione and the like. In the embodiment wherein both spiro rings have a fused cyclic substituent, i.e., adjacent Z groups on both rings are Z'', exemplary spirodilactams include 1,6di(4-hydroxyphenyl)-3,4,8,9-dibenzo-1,6-diazaspiro[4.4]nonane-2,7-dione, 1,6-di(3-hydroxyphenyl)-3,4,8,9-di(pyrido)-1,6-diazaspiro[4.4]nonane-2,7-dione, 1,6-di[4-(4-hydroxyphenyloxy)phenyl]-3,4,8,9-di(cyclopentano)-1,6-diazaspiro[4.4]nonane-2,7-dione and the like. Also suitable are those spirodilactams in which one spiro ring has a fused cyclic substituent and the other spiro ring is free of fused cyclic substituents, e.g., 1,6-di (4-hydroxyphenyl)-3,4-benzo-8-methyl-1,6-diazaspiro[4.4]nonane-2,7-dione, 1,6-di[1(4-hydroxynaphthyl)]-3,4-cyclopentano-1,6-diazaspiro[4.4]nonane-2,7-dione and the like.

In general, the spirodilactams of formula I wherein R and R' are aromatic and hydrocarbyl are preferred and further preferred are those compounds wherein each r is 0. The class of compounds wherein R is phenylene, i.e., the 1,6-di(hydroxyphenyl) spirodilactams, is particularly preferred, especially the 1,6-di(4-hydroxyphenyl) spirodilactams. Within the spirodilactam ring portion of the molecule, compounds wherein both spiro rings are free of fused cyclic substituents are preferred as are the spirodilactams wherein both spiro rings have a fused cyclic substituent. The compound 1,6-di(4-hydroxyphenyl)-1,6-diazaspiro[4.4]nonane-2,7-dione is an especially preferred member of the former class and 1,6-di(4-hydroxyphenyl)-3,4,8,9-dibenzo-1,6-diazaspiro[4.4]nonane-2,7-dione is especially preferred member of the latter class.

The hydroxyaryl-substituted spirodilactams of formula I are compounds which are described in more detail and claimed as compositions of matter in copending allowed U.S. patent application Ser. No. 245,618, filed Sept. 16, 1988. The general method for the production of the hydroxyaryl-substituted spirodilactams, also described and claimed in this copending application as well as U.S. Pat. No. 4,889,907, which is incorporated herein by reference, is by reaction of at least one hydroxy-containing primary amino compound and a precursor of the spirodilactam. In terms of the spirodilactams of formula I, the hydroxy-containing primary amino compound precursor is of the formula $$HO-R-(X-R')_r-NH_2 \qquad (II)$$

wherein R, R', r and X have the previously stated meanings. The spirodilactam precursor is a 4-oxoheptandioic acid compound or a spirodilactam of corresponding [4.4]structure with lactone oxygens in the 1- and 6- spiro ring positions. In terms of the spirodilactam of formula I, the 4-oxoheptanedioic acid compound is represented by the formula

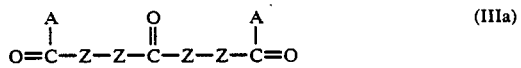

wherein Z has the previously stated meaning and A independently is hydroxy, lower alkoxy of up to 4 carbon atoms or halo, preferably middle halo. The spirodilactone precursor of the spirodilactams is represented by the formula

where Z has the previously stated meaning.

The hydroxy-containing amino compound precursr (formula II) and the spirodilactam precursor (formula IIIa or IIIb) react in a 2:1 molar ratio at an elevated temperature in liquid phase solution in an inert reaction diluent, for example an N-alkylamide such as N,N-dimethylacetamide, N-methyl-2-pyrrolidone or the like. A reaction temperature of from about 80° C. to about 250° C. is typical and the reaction pressure is sufficient to maintain the reaction mixture in the liquid phase. Reactant contact is maintained during reaction by conventional methods such as shaking or stirring and subsequent to reaction the hydroxyaryl-substituted spirodilactam is recovered by well known techniques such as precipitation followed by filtration or decantation or by solvent removal. Recovery of the substituted spirodilactam is not required, however, particularly when substantially stoichiometric quantities of hydroxy-containing amino compound and the spirodilactam precursor were employed, and the hydroxyaryl-substituted spirodilactam can be further reacted in situ.

The epoxyalkyl derivative of the spirodilactam which is a component of the compositions of the invention is produced by reaction of the spirodilactam of formula I with a 1-halo-2,3-epoxyalkane, preferably of up to 8 carbon atoms inclusive. The halo moiety is fluoro, chloro, bromo or iodo but is preferably middle halogen, i.e., chloro or bromo. Illustrative haloepoxyalkane reactants include epichlorohydrin, epibromohydrin, 1-chloro-2,3-epoxyhexane, 1-bromo-2,3-epoxybutane, 1-chloro-2-methyl-2,3-epoxypropane, 1-bromo-2,3-epoxyoctane and the like. The chloroepoxyalkanes are generally preferred over the corresponding bromoepoxyalkanes and epihalohydrins are preferred over the other haloepoxyalkanes. A particularly preferred haloepoxyalkane reactant is epichlorohydrin.

The hydroxyaryl-substituted spirodilactam of formula 1 and the haloepoxyalkane are reacted by employing the conventional methods normally utilized in the production of epoxyalkyl derivatives, particularly glycidyl derivatives of polyhydroxylic compounds such as 2,2-di(4-hydroxyphenyl) propane. The haloepoxyalkane reactant is provided in a molar ratio of at least 2:1 relative to the quantity of substituted spirodilactam and frequently in a substantially higher ratio to permit the haloepoxyalkane to serve as a reaction diluent as well as a reactant. Alternatively, other reaction diluents are employed such as an alkylated benzene, e.g., toluene or xylene, so long as the diluent is capable of dissolving at least a portion of each reactant and is inert towards the reactants and the epoxyalkyl-substituted product. The epoxyalkyl spirodilactams are produced by contacting the haloepoxyalkane and spirodilactam reactants under reaction conditions including a reaction temperature of from about 80° C. to about 180° C. and a reaction pressure of from about 1 atmosphere to about 10 atmospheres. This initial reaction produces a reaction intermediate, which, without isolation, is treated with at least a stoichiometric quantity of a strong base, typically aqueous sodium hydroxide or potassium hydroxide, while the water formed or present is removed by distillation under conditions of approximately the normal boiling temperature of the mixture at ambient pressure.

Particularly good results are obtained when the reaction of the haloepoxyalkane and the substituted spirodilactam is conducted in the presence of a quaternary phosphonium or ammonium salt as catalyst, particularly those phosphonium or ammonium salts in which the substituents on the phosphorus or nitrogen are lower alkyl or phenyl. Alkyltriphenylphosphonium salts, particularly ethyltriphenylphosphonium iodide or bromide, are a preferred class of the quaternary phosphonium salts to be used as catalyst. This two-step process is entirely conventional for the conversion of hydroxyphenyl compounds to the corresponding glycidyloxy derivatives by reaction with epichlorohydrin. For example, 2,2-di(4-hydroxylhenyl)propane is converted commercially to the corresponding diglycidyl ether by this technique.

The epoxyalkyl-substituted spirodilactams which are a component of the compositions of the invention are epoxyalkyl derivatives illustratively produced by replacement of each hydroxylic hydrogen of the hydroxyaryl-substituted spirodilactam with a 1-(2,3-epoxy)alkyl moiety. In terms of the spirodilactam reactant of formula I, the epoxyalkyloxyaryl-substituted spirodilactam products are represented by the formula

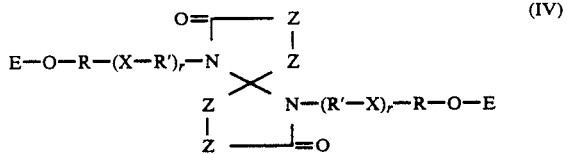  (IV)

wherein E independently is 1-(2,3-epoxy)alkyl of up to 8 carbon atoms inclusive and R, R', r and Z have the previously stated meanings.

The identity of specific epoxyalkyl-containing spirodilactams of the above formula IV will be apparent from the above description and formula for the reactants and the formula for the products. Exemplary epoxyalkyl-containing spirodilactam products include 1,6-di(4-glycidyloxyphenyl)-1,6-diazaspiro[4.4]nonane-2,7-dione, illustratively produced from epichlorohydrin and 1,6-di(4-hydroxyphenyl)-1,6-diazaspiro4.4nonane-2,7-dione, 1,6-di[4-(3-glycidyloxyphenyloxy)phenyl]-1,6-diazaspiro[4.4]nonane-2,7-dione illustratively produced by reaction of epibromohydrin and 1,6-di[4-(3-hydroxyphenyloxy)phenyl]-1,6-diazaspiro[4.4]nonane-2,7-dione and 1,6-di[4-(2,3-epoxybutyloxy)phenyl]-3,4,8,9-di(benzo)-1,6-diaza[4.4]nonane-2,7-dione illustratively produced from 1-chloro-2,3-epoxybutane and 1,6-di(4-hydroxyphenyl)-3,4,8,9-dibenzo-1,6-diazaspiro[4.4]nonane-2,7-dione.

These epoxyalkyloxyaryl-substituted spirodilactams (formula IV) are described in more detail and are claimed as compositions of matter in U.S. Pat. No. 4,895,942, which is incorporated herein by reference.

The remainder of the compositions of the invention comprise at least one amine compound having at least two amino hydrogen substituents. The amine compound is aliphatic, aromatic or mixed aliphatic and aromatic and is a monoamine, which has at least one primary amino group, i.e., —NH₂, or is a di- or polyamine, which has at least two primary or secondary amino groups, i.e., >N—H groups.

Amine compounds include butylamine, aniline, tetramethylenediamine, hexamethylenediamine, 1,4-diaminopentane, diethylenetriamine, 2-amino-2-isopropylaminopropane, 1,3-diaminocyclohexane, N-aminoethylpiperazine. N,N-dimethyl-p-phenylenediamine, bis(N-sec-butyl-4-aminophenyl)amine, and the like.

In one embodiment the preferred amine compounds are aromatic primary monoamines including aniline, 2,6-dimethylaniline, 2,4-dimethylaniline, 2,6-diethylaniline, 2,6-diisopropylaniline, tolylamine, 2-naphthylamine, 1-aminoadamantane, norbornylamine and the like. The preferred primary monoamine is aniline. In another embodiment, (he preferred amine compounds are aromatic primary diamines and particularly preferred are the diamines

  (V)

wherein R and r have the previously stated meaning and X' is a direct valance bond, alkylene of up to 8 carbon atoms inclusive, oxy, thio, sulfonyl, carbonyl and dialkylenebenzene. Illustrative aromatic diamine compounds are p-phenylenediamine, 3,3'-diaminohiphenyl, di(4-aminolphenyl) ether, di(4-amino-3-methylphenyl) sulfone, 2,2-di(4-aminophenyl)propane, di(4-aminophenyl)methane, di(4-aminophenyl)sulfone, di(4-amino-3,5-dimethylphenyl)methane, di(3-amino-4-chlorophenyl)methane, 2,4-diaminotoluene, sulfanilamide, p-aminobenzamide, 1,4-di(4-amino-3-methylphenylmethyl)benzene, 4,4'-diamino-3,3',5,5'-tetramethylbiphen),1, 1,4-di(4-amino-3,5-dimethylphenylisopropyl)benzene, di(3-aminophenyl) sulfide, di[1-(5-aminonaphthyl)]methane, m-phenylenediamine, di(4-amino-3-bromophenyl)methane and the like.

The generally preferred diamine compounds of formula V are those wherein each R is phenylene, preferably p-phenylene, and r is 1. The diamine compounds di(4-aminophenyl)sulfone and 1,4-di(4-amino-3,5-dimethylphenylisopropyl)benzene are particularly preferred amine compounds of the compositions of the invention.

The preferred compositions of the invention comprise the epoxyalkyloxyaryl-substituted spirodilactams of formula IV and at least one aromatic amine compound. The precise proportions of the compositions of the invention are not critical although in general stoichiometric proportions of the amine compound and the epoxy-substituted spirodilactams are used. Compositions of at least about 60% by weight based on total composition of the epoxyalkyloxyaryl-substituted spirodilactam are preferred, with further preference given to compositions of at least about 70% by weight on the same basis, with the remainder being at least one amine compound. Compositions having as many as three amine compounds, present in approximately equal proportions by weight, are satisfactory although the preferred compositions are of an epoxyalkyloxyaryl-substituted spirodilactam and a single aromatic mono- or diamine compound. It is also possible to include within the compositions minor amounts of other epoxy-substituted compounds, but preferred compositions contain the epoxyalkyloxyarylsubstituted spirodilactam as substantially the sole epoxy-containing material present.

The compositions of the invention are produced by forming an intimate mixture of the substituted spirodilactam and the amine compound. The method of mixing is not critical and conventional methods of blending, stirring or co-melting the components are satisfactory, provided that the mixing does not result in sufficient heat to cause the cure or crosslinking of the partially mixed composition.

The curing of the thermosetting resin composition is by application of heat. The curing or crosslinking is usually conducted by heating the composition to a curing temperature of above about 125° C. but generally below about 300° C. and preferably from about 150° C. to about 250° C. It is often desirable to carry out the curing process in two stages. Initially, in a first stage, the composition is heated to a relatively low curing temperature of from about 150° C. to about 175° C. for a time sufficient to initiate the curing process. The partially cured product is then heated to a higher temperature, e.g., for about 180° C. to about 250° C., to complete the cure. The cured products are highly crosslinked solids having relatively high glass transition temperature and good properties of strength and rigidity and resistance to common soluents. The compositions are processed by methods which are conventional for the curing of thermosetting resins to produce cured compositions which are useful in adhesive formulations and in coating and structural applications for the aerospace and electronic industries.

The invention is further illustrated by the following Illustrative Embodiments which should not be construed as limiting the invention.

ILLUSTRATIVE EMBODIMENT I

A mixture of 10.14g (0.03 mole) of 1,6-di(4-hydroxyphenyl)-1,6diazaspiro-4.4]nonane-2,7-dione, 0.05g of ethyltriphenylphosphonium bromide and 150 ml of epichlorohydrin was placed in a 500 ml round-bottom flask equipped with a mechanical stirrer and a condenser. The mixture was stirred and warmed to 120° C. and maintained at 110° C. to 120° C. for 4 hours. The mixture was then cooled to 80°-90° C. while stirring continued and 5.0 g of 50% by weight aqueous sodium hydroxide was added dropwise as the water present or formed was removed by distillation. After the addition of the sodium hydroxide was complete, unreacted epichlohydrin was removed by distillation under reduced pressure and methanol was added to precipitate the product. The precipitated product was washed several times with methanol and dried in a vacuum oven for 24 hours. The product had a melting point of 170° C. and the nuclear magnetic spectra were consistent with the structure 1,6-di(4-glycidyloxyphenyl)-1,6-diazaspiro4.4]nonane-2,7-dione. The isolated yield was greater than 95%.

ILLUSTRATIVE EMBODIMENT II

A mixture of 82 parts by weight of 1,6-di(4-glycidyloxyphenyl)-1,6-diazaspiro[4.4]nonane-Z,7-dione and 18 parts by weight of di(4-aminophenyl)methane was melted at 130°-150° C. The mixture was then heated in an oven at a first stage of 150° C. for 2 hours and in a second stage at 200° C. for an additional 2 hours. The resulting cured product, upon cooling, was found to have a glass-transition temperature of 185° C.

ILLUSTRATIVE EMBODIMENT III

A mixture of 72 parts by weight of 1,6-di(4-glydicyloxyphenyl)-1,6-diazaspiro[4.4]nonane-1,6-dione and 22 parts by weight of di(4-aminophenyl)sulfone was melted at 150°-170° C. The mixture was then heated in an oven at a first stage for 175° C. for 2 hours and in a second stage at 200° C. for an additional 2 hours. The resulting cured product, upon cooling, was found to have a glass transition of 220° C.

ILLUSTRATIVE EMBODIMENT IV

A mixture of 70 parts by weight of 1,6-di(4-glycidyloxyphenyl)-1,6-diazaspiro[4.4]nonane-2,7-dione and 30 parts of 1,4-di[2-(4-amino-3,5-dimethylphenyl)isopropyl]benzene was melted at 170°-180° C. The resulting mixture was heated in an oven at a first stage of 150° C. for 2 hours and in a second stage at 200° C. for an additional 4 hours. The cured product, upon cooling, was found to have a glass transition temperature of 243° C.

ILLUSTRATIVE EMBODIMENT V

A mixture of 84 parts by weight of 1,6-di(4-glycidyloxylphenyl)-1,6-diazaspiro[4.4]nonane-2,7-dione and 16 parts by weight of sulfanilamide was melted at 160°-170° C. The resulting mixture was heated in an oven at a first stage of 175° C. for 2 hours and in a second stage at 200° C. for an additional 2 hours. The resulting cured product, upon cooling, was found to have a glass transition temperature of 219° C.

ILLUSTRATIVE EMBODIMENT VI

A mixture of 78 parts by weight of 1,6-di(3-glycidyloxyphenyl)-1,6-diazaspiro[4.4]nonane-2,7-dione and 22 parts by weight of di(4-aminophenyl)sulfone was melted at 140°-150° C. The resulting mixture was heated in an oven at a first stage of 175° C. for 2 hours and in a second stage at 200° C. for an additional 2 hours. The resulting cured product, upon cooling, was found to have a glass transition temperature of 221° C.

ILLUSTRATIVE EMBODIMENT VII

Following procedures described in Embodiments II-VI above, a mixture of 1,6-di(4-glycidyloxlphenyl)-1,6-diazaspiro[4.4]nonane-2,7-dione and aniline are heated for several hours to give a cured product.

ILLUSTRAIVE EMBODIMENT VIII

Following procedures described in Embodiments II-VI above, a mixture of 1,6-di(4-glycidyloxyphenyl)-1,6-diazaspiro4.4]nonane-3,7-dione and N,N-dimethyl-p-phenylenediamine are heated for several hours to give a cured product.

ILLUSTRATIVE EMBODIMENT IX

Following procedures described in Embodiments II-VI above, a mixture of 1,6-di(4-glycidyloxylphenyl)-1,6-diazaspiro4.4]nonane-2.7-dione and diethyltriamine are heated for several hours to give a cured product.

What is claimed is:

1. A curable thermosetting resin composition comprising (1) an epoxyalkyl ether of a 1,6-diaza[4.4]-spirodilactam having a hydroxyaryl-containing substituent on each spiro ring nitrogen atom and (2) an amine compound having at least two amino hydrogen substituents.

2. The composition of claim 1 wherein the ether is represented by the formula

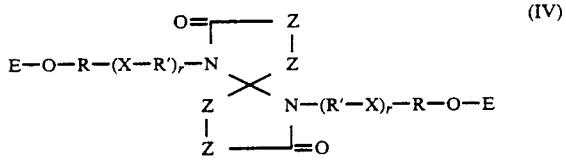      (IV)

wherein E independently is 1-(2,3-epoxy)alkyl of up to 8 carbon atoms, inclusive, R is aromatic of up to 15 carbon atoms and up to two aromatic rings, inclusive, R' is R or aliphatic of up to 10 carbon atoms, inclusive, X is a direct valence bond, alkylene of up to 8 carbon atoms inclusive, oxy, thio, sulfonyl, carbonyl, dioxyphenylene, 2,2-di(oxyphenyl)propane, di(oxyphenyl)sulfone or dioxydiphenylene, r is 0 or 1 and Z independently is $>C(Z')_2$ in which Z' independently is hydrogen, lower alkyl, lower halo or phenyl, or Z is such that adjacent Z groups taken together form a ring system Z'' of from 5 to 7 ring atoms up to two of which are heteroatoms selected from nitrogen, oxygen or sulfur with the remainder of the ring atoms being carbon atoms, there being up to 15 carbon atoms In each Z'', two of which connect the keto and spiro carbon atoms connected by the adjacent Z groups.

3. The composition of claim 2 wherein the amine compound is a primary monoamine.
4. The composition of claim 3 wherein E is glycidyl.
5. The composition of claim 4 wherein each R' is R.
6. The composition of claim 5 wherein each R is phenylene.
7. The composition according to any one of claims 2, 3, 4, 5 or wherein, in the ether, each r is 0.
8. The composition of claim 7 wherein each Z is $>C(Z')_2$.
9. The composition of claim 8 wherein Z' is hydrogen.
10. The composition of claim 9 wherein each R is p-phenylene.
11. The composition of claim 10 wherein the amine compound is an aromatic mono-amine.
12. The composition of claim 10 wherein the amine compound is aniline.
13. The composition of claim 10 wherein the amine compound is diethylenetriamine.
14. The composition of claim 7 wherein adjacent Z groups in each spiro ring are Z''.
15. The composition of claim 14 wherein each R is p-phenylene.
16. The composition of claim 14 wherein Z'' is benzo.
17. The cured product obtained by heating the composition of claim 1 to a curing temperature above 125° C.
18. The cured product obtained by heating the composition of claim 12 to a curing temperature above 125° C.

* * * * *